United States Patent
Tsuchida et al.

(10) Patent No.: US 10,131,917 B2
(45) Date of Patent: *Nov. 20, 2018

(54) HIGHLY EFFICIENT ETHANOL-FERMENTATIVE YEAST

(71) Applicant: HONDA MOTOR CO., LTD., Tokyo (JP)

(72) Inventors: Yoshiki Tsuchida, Saitama (JP); Ikumi Kurihara, Saitama (JP); Tomohiro Imai, Saitama (JP); Iku Koike, Saitama (JP)

(73) Assignee: HONDA MOTOR CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/532,725

(22) PCT Filed: Dec. 5, 2014

(86) PCT No.: PCT/JP2014/082336
§ 371 (c)(1),
(2) Date: Jun. 2, 2017

(87) PCT Pub. No.: WO2016/088278
PCT Pub. Date: Jun. 9, 2016

(65) Prior Publication Data
US 2017/0327831 A1   Nov. 16, 2017

(51) Int. Cl.
| | | |
|---|---|---|
| *C12N 15/81* | (2006.01) |
| *C12N 1/16* | (2006.01) |
| *C12N 7/06* | (2006.01) |
| *C12N 1/20* | (2006.01) |
| *C12P 7/06* | (2006.01) |
| *C12N 9/04* | (2006.01) |
| *C12N 9/10* | (2006.01) |
| *C12P 7/10* | (2006.01) |

(52) U.S. Cl.
CPC ............. *C12N 15/815* (2013.01); *C12N 1/20* (2013.01); *C12N 9/0006* (2013.01); *C12N 9/1022* (2013.01); *C12P 7/06* (2013.01); *C12P 7/10* (2013.01); *C12Y 101/01001* (2013.01); *C12Y 202/01002* (2013.01); *Y02E 50/17* (2013.01)

(58) Field of Classification Search
None
See application file for complete search history.

(56) References Cited

U.S. PATENT DOCUMENTS

| | | |
|---|---|---|
| 2012/0282664 A1 | 11/2012 | Kondo et al. |
| 2013/0189788 A1 | 7/2013 | Zhang et al. |
| 2017/0349917 A1* | 12/2017 | Tsuchida .................. C12P 7/06 |

FOREIGN PATENT DOCUMENTS

| | | |
|---|---|---|
| JP | 2011-24500 | 2/2011 |
| JP | 2011-50359 | 3/2011 |
| JP | 2012-170422 | 9/2012 |
| JP | 2014-158437 | 9/2014 |
| WO | 2011/065539 | 6/2011 |

OTHER PUBLICATIONS

International Search Report dated Mar. 17, 2015 (dated Mar. 17, 2015), Application No. PCT/JP2014/082336, 4 pages.
Chao Fan et al., "Efficient ethanol production from corncob residues by repeated fermentation of an adapted yeast", Bioresource Technology (2013), pp. 309-315, vol. 136, 7 pages, Shanghai, China.
Angela Cristina Schirmer-Michel et al., "Production of ethanol from soybean hull hydrolysate by psmotolerant Candida guilliermondii NRRL Y-2075", ScienceDirect, Bioresource Technology (2008), pp. 2898-2904, vol. 99, 7 pages, Porto Alegre, RS, Brazil.
Itsuki Watanabe et al., "Ethanol production by repeated-batch simultaneous saccharification and fermentation (SSF) of alkali-treated rice straw using immobilized *Saccharomyces cerevisiae* cells", Bioresource Technology (2012), pp. 695-698, vol. 123, 4 pages, Kanagawa, Japan.
Han Li-Li et al., "Breeding of Higher Ethanol Fermentation of Xylose Strain with Protoplast Fusion and Mutagenisis", Liquor Making, Mar. 2008, vol. 35, No. 2, pp. 38-41, 4 pages, Beijing, China.
T. Granstrom et al., "Chemostat study of xylitol production by Candida guilliermondii", Appl Microbiol Biotechnol (2001), vol. 55, pp. 36-42, 7 pages, Kantvik, Finland.
Paul A. Bicho et al., "Induction of Xylose Reductase and Xylitol Dehydrogenase Activities in Pachysolen tannophilus and Pichia stipitis on Mixed Sugars", Applied and Environmental Microbiology, Jan. 1988, vol. 54, No. 1, pp. 50-54, 5 pages, Ontario, Canada.
Cesar Fonseca et al., "L-Arabinose metabolism in Candida arabinofermentans PYCC 5603T and Pichia guilliermondii PYCC 3012: influence of sugar and oxygen on product formation", Appl Microbiol Biotechnol (2007), vol. 75, pp. 303-310, 8 pages, Caparica, Portugal.
European Search Report dated Mar. 26, 2018, 5 pages.
Min Zhang et al., "Metabolic Engineering of a Pentose Metabolism Pathway in Ethanologenic Zymomonas mobilis", Science, Jan. 13, 1995, vol. 267, pp. 240-243, English text, 6 pages.

* cited by examiner

*Primary Examiner* — Channing S Mahatan
(74) *Attorney, Agent, or Firm* — Rankin, Hill & Clark LLP

(57) ABSTRACT

An object of the present invention is to obtain a fermentative yeast having a highly efficient ethanol production without introducing a foreign gene. A further object is to obtain a fermentative yeast that is resistant to proliferation inhibitors such as organic acids, which prevent the proliferation of the fermentative yeast. A yeast having an improved ethanol production ability was generated by introducing transaldolase and alcohol dehydrogenase genes by self-cloning to *Meyerozyma guilliermondii* that can produce ethanol effectively from pentose and hexose obtained by breeding, and further breeding the resultant yeast.

2 Claims, 4 Drawing Sheets
Specification includes a Sequence Listing.

HIGHLY EFFICIENT ETHANOL-FERMENTATIVE YEAST

TECHNICAL FIELD

The present invention relates to a yeast for fermenting a saccharified solution in bioethanol production using lignocellulosic biomass.

In particular, the present invention relates to a yeast capable of effectively producing ethanol from pentose (which may be, hereinafter, also referred to as C5) and hexose (which may be, hereinafter, also referred to as C6) in bioethanol production using lignocellulosic biomass.

BACKGROUND ART

Bioethanol is expected to be a renewable resource that is produced by biomass. Moreover, since carbon dioxide that is produced by combustion of bioethanol is carbon neutral, increased use of bioethanol is considered to suppress increase of carbon dioxide, which is a main cause of the global warming.

Bioethanol is obtained by fermenting biomass and distilling and purifying ethanol. It is necessary to produce much alcohol from saccharified solutions for increasing the yield of bioethanol. Since the yeasts generally used in the process of bioethanol production cannot convert pentose such as xylose and arabinose into alcohol, only hexose has been used as raw materials for fermentation.

Typical biomass is reported to contain 35-45% of cellulose, 25-40% of hemicellulose, and 15-30% of lignin, though the contents vary according to raw materials. Therefore, use of hemicellulose, which mainly contains the pentose xylose, but not only cellulose, which is a polymer of hexose, as a substrate should lead to effective ethanol production.

Xylose is reported to be the second abundant sugar in biomass next to glucose and it is an important object in bioethanol production to use pentose effectively.

Techniques for using xylose, even at a little amount, by imparting the ability to utilize xylose by genetic recombination, using microorganism that produces ethanol from xylose, or the like have been so far disclosed.

Patent Literature 1 discloses an invention involving converting xylose (C5) into xylulose by introducing a gene having the xylose transporter activity into a host cell to incorporate it in the pentose phosphate pathway of the glycolysis and use it for fermentation.

Patent Literature 2 discloses a technique for producing alcohol with yeast provided with an arabinose transporter. This involves incorporation of arabinose (C5) via arabitol and xylulose in the pentose phosphate pathway in the glycolysis to use it for fermentation, similar to the invention of Patent Literature 1.

Non-Patent Literature 1 discloses provision of xylose utilization ability by incorporating a xylose utilization gene derived from *Escherichia coli* in *Zymomonas*.

Non-Patent Literature 2 describes production of ethanol from xylose by yeast in the genus *Pichia*.

CITATION LIST

Patent Literature

Patent Literature 1:
Japanese Patent Laid-Open No. 2012-170422
Patent Literature 2:
U.S. Patent Application Publication No. 2013/189788

Non Patent Literature

Non Patent Literature 1:
Zhang, M., et al., Science, 1995. Vol. 267, pp. 240-243.
Non Patent Literature 2:
Bicho, P. A., et al., Appl. Environ. Microbiol., 1988, Vol. 54, pp. 50-54.

SUMMARY OF INVENTION

Technical Problem

However, the invention of Patent Literature 1 involves introducing a protein having the xylose transporter activity derived from *Candida guilliermondii* into *Saccharomyces cerevisiae* as a host. Accordingly, a foreign gene would be introduced.

The invention of Patent Literature 2 is also an invention involving introduction of a gene from a species different from the host, although the transporter gene is different.

The technique described in Non-Patent Literature 1 also involves introduction of a xylose utilization gene. The technical concept thereof is different from Patent Literature 1 and 2 described above, but they are similar in that a foreign gene is introduced.

Therefore, any of the inventions described in Patent Literature 1 and 2 and Non-Patent Literature 1 requires adopting a containment measure to comply with "the Cartagena Protocol on Biosafety to the Convention on Biological Diversity" adopted in the United Nations. Accordingly, they require facilities for ensuring the biosafety and therefore it is disadvantageous in cost to produce ethanol using such yeasts.

Moreover, use of yeast in the genus *Pichia* by the technique described in Non-Patent Literature 2 does not result in a much higher efficiency of ethanol production because the low xylose availability in the wild-type *Pichia* yeast.

An object of the present invention is to obtain a fermentative yeast having a highly efficient ethanol production without introducing a foreign gene.

Solution to Problem

The present invention features *Meyerozyma guilliermondii* effectively producing ethanol from pentose and hexose, wherein the fermentative yeast has an ethanol production with a corn stover sugar solution improved by breeding a yeast deposited to NITE Patent Microorganisms Depositary (#122, 2-5-8 Kazusakamatari, Kisarazu-shi, Chiba 292-0818, Japan) on Dec. 4, 2014 under the accession number NITE ABP-01976 (hereinafter, also referred to as strain ABP-01976) in a corn stover sugar solution.

The strain ABP-01976 is a yeast in which transaldolase and alcohol dehydrogenase are self-cloned into a highly efficient ethanol-fermentative yeast obtained by breeding in a sugar solution derived from rice straw and selecting yeasts having high fermentation yield to increase fermentation yield.

However, its fermentation yield in sugar solutions derived from corn stover is not very high since it was bred and selected with sugar solution derived from rice straw. Therefore, a yeast having an improved fermentation yield was obtained by conducting breeding in sugar solution derived from corn stover.

The highly efficient ethanol-fermentative yeast according to the present invention is characterized by being *Meyerozyma guilliermondii* that effectively produces ethanol from pentose and hexose and being deposited to NITE Patent Microorganisms Depositary (#122, 2-5-8 Kazusakamatari, Kisarazu-shi, Chiba 292-0818, Japan) on Nov. 19, 2014 under the accession number NITE BP-01966 (hereinafter, also referred to as strain BP-01966).

A yeast having an especially high fermentation yield among the yeasts that were acclimated to a corn stover sugar solution by conducting breeding in a sugar solution derived from corn stover and had improved fermentation yield was deposited to NITE Patent Microorganisms Depositary to obtain the accession number NITE BP-01966.

The yeast according to the present invention is a yeast obtained by breeding and recombination introducing enzyme genes of *Meyerozyma guilliermondii* itself and does not require any containment measure to comply with the Cartagena Act. Therefore, conventional facilities can be used without needing special facilities for biosafety.

DESCRIPTION OF EMBODIMENTS

Figure 1:
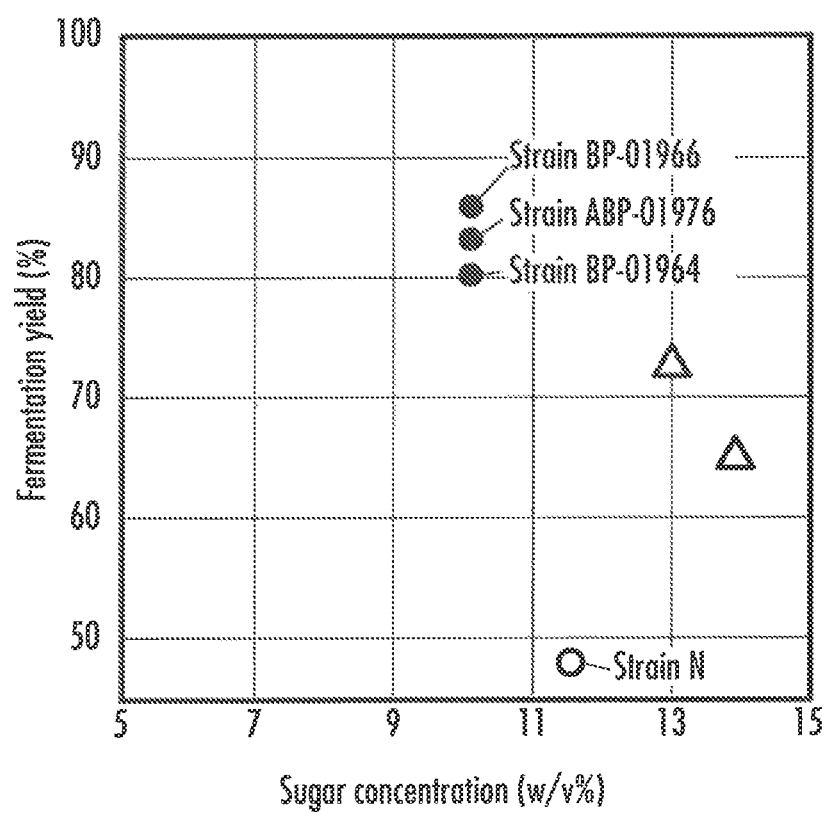
FIG. 1 illustrates fermentation yields of the parent strain (the strain N), the strain BP-01964, the strain ABP-01976, and BP-01966, the yeast strain according to the present invention.

The yeast strain according to the present invention is described below.

EXAMPLES

1. Isolation of Strain

Strains having a high ethanol production ability were selected by breeding of the parent strain (the strain N) of *Meyerozyma guilliermondii* using a sugar solution derived from rice straw. Rice straw from Kumagaya, Japan was immersed in an equal amount of a 25% ammonium solution at 80° C. for 3 hours and then ammonia was allowed to evaporate. The pH of the treated biomass was adjusted to 4 and then *Acremonium* cellulase (manufactured by Meiji Seika Pharma Co., Ltd.) was added to conduct enzymatic saccharification at 50° C. for 72 hours. The solid-liquid separation of the produced slurry was conducted by filter-pressing to collect the liquid. Using this liquid (hereinafter, also referred to as clear liquid), habituation in culture was conducted with addition of a mutagen for 19 months and strains with improved fermentation performance were selected. Strains having improved fermentation performance were selected based on the amount of ethanol produced after a certain period of time. A strain with high fermentation performance was deposited to NITE Patent Microorganisms Depositary, National Institute of Technology and Evaluation (Independent Administrative Institution) under the accession number NITE BP-01964.

It has been confirmed, although it is not shown here, that the yeast strain BP-01964 is a strain that produces ethanol more than twice as much as the wild type does and that, not only the ability to utilize glucose, which is C6, but also the ability to utilize xylose, which is C5, is improved.

Next, a yeast having an even higher ethanol production ability was obtained by introducing transaldolase and alcohol dehydrogenase genes into the yeast strain BP-01964 by self-cloning.

Fermentation inhibitors such as organic acids, aldehyde, and phenol are produced as by-products when liquids derived from rice straw treated with ammonia is used and treated with a saccharification enzyme to obtain a sugar solution. In particular, acetic acid is present at a very high amount as much as about 1,000 mg/L and reduces the fermentation yield. Therefore, by suppressing the inhibition of fermentative yeast proliferation with acetic acid, the ethanol production efficiency can be further improved.

Transaldolase is an enzyme that catalyzes metabolism from sedoheptulose-7-phosphate (S7P) and glyceraldehyde-3-phosphate (GAP) to erythrose-4-phosphate (E4P) and fructose 6-phosphate (F6P) in the pentose phosphate pathway, which is branched from the glycolysis. It has been confirmed that introduction of this enzyme increases the ethanol yield in the presence of the inhibitor acetic acid.

The xylose reductase promoter was ligated in the upstream of the transaldolase. This is because transaldolase is considered to work efficiently when using the promoter of xylose reductase that functions in the xylose utilization.

Alcohol dehydrogenase is an enzyme that can produce ethanol from acetaldehyde and that can convert aldehyde contained as an inhibitor in a rice straw sugar solution and reduce its toxicity.

The GAPDH promoter was ligated in the upstream of the alcohol dehydrogenase. Since the glyceraldehyde-3-phosphate dehydrogenase (GAPDH) prompter is a strong promoter that functions in the glycolysis, it is considered to be an efficient prompter for use as a promoter of alcohol dehydrogenase, which is an enzyme in the glycolysis.

Therefore, generation of a recombinant fermentative yeast into which the 2 enzymes are introduced by genetic introduction can be expected to produce a yeast having a higher ethanol production ability.

The genetic introduction was conducted by the following procedure. Amplify the gene to be transferred and a terminator region thereof (hereinafter, referred to as gene+terminator region) by PCR. Amplify by PCR the promoter region used for the introduction. These should be both amplified by PCR from the chromosomes of the strain of *Meyerozyma guilliermondii* used in the present invention.

Clone the DNA fragments amplified by PCR into a commercially available vector for *Escherichia coli* by infusion in the order of promoter, gene+terminator region. Transform *Escherichia coli* with the cloned vector and amplify the vector. Obtain DNA fragments for homologous recombination by cutting out the promoter and gene+terminator region from the amplified vector with restriction enzymes or amplifying the promoter and gene+terminator region from the amplified vector by PCR.

The xylose reductase promoter was amplified with the following primers of SEQ ID NO: 1 and SEQ ID NO: 2 and the transaldolase gene and the terminator region were amplified with the primers of the following SEQ ID NOs: 3 and 4.

SEQ ID NO: 1:
AAGGCTTGGGAACTTTCTTT

SEQ ID NO: 2:
AGCAATTGATGATTAATTTT

SEQ ID NO: 3:
ATGACCAATTCTCTTGAACA

SEQ ID NO: 4:
AAATTGTGCCGTGTCAAACT

Specifically, the GAPDH prompter was amplified with the primers of the following SEQ ID NO: 5 and SEQ ID NO: 6 and the alcohol dehydrogenase gene and the terminator region were amplified with the primers of the following SEQ ID NOs: 7 and 8.

SEQ ID NO: 5:
GTTGTAGCGGAGGCTCAATT

SEQ ID NO: 6:
TGTATAATTTAAATGTGGGT

SEQ ID NO: 7:
ATGTCAATTCCAGAATCCAT

SEQ ID NO: 8:
CACCTTGGCTGGAAGTGCTG

The homologous recombination of the obtained DNA fragments into the yeast strain was performed to obtain desired strains. Electroporation was used for the homologous recombination. The DNA fragments for the homologous recombination were the xylose reductase promoter, transaldolase+terminator, the GAPDH promoter, and alcohol dehydrogenase+terminator, in this order. Moreover, while the strains obtained by this method comprise introduced genes, they belong to a category to be treated as a non-modified yeast under the Cartagena Act because they are self-cloned.

A yeast having a high ethanol production ability was isolated from the yeast strains in which genes have been introduced and deposited to NITE Patent Microorganisms Depositary to obtain the accession number NITE ABP-01976.

Next, a yeast strain having a high fermentation yield in a sugar solution derived from corn stover was obtained by conducting 4 months habituation in culture in a sugar solution derived from corn stover and deposited to NITE Patent Microorganisms Depositary under the accession number BP-01966. The properties such as fermentation yield of the obtained yeast strain are described below.

2. Properties of the Yeast Strain
2.1 Fermentation Yield

Fermentation tests of the parent strain and the strain according to the present invention were conducted. Plural enzymatically saccharified solutions having different sugar concentrations derived from corn stover treated with dilute sulphuric acid and adjusted to pH 6 were used and a liquid culture of the aforementioned strain was added so that the $OD_{600}$ of the medium became 2.0. The concentrations of ethanol obtained after culturing at 30° C. for 96 hours and the fermentation yields calculated from the sugar concentration of the used saccharified solution were plotted. The result is shown in FIG. 1.

As shown in FIG. 1, while the fermentation yield of the strain N, the parent strain, was about 48%, the fermentation yield of the high ethanol production strain BP-01964 obtained by breeding was 80%, the fermentation yield of the strain ABP-01976, obtained by genetic recombination introducing transaldolase and alcohol dehydrogenase was 84%, and the fermentation yield of the strain accession number BP-01966 according to the present invention obtained by breeding in a sugar solution derived from corn stover was even higher and about 86%. It is also apparent that the strain according to the present invention exhibits a high fermentation yield in comparison with the fermentation yields of the fermentative yeasts from other companies, represented by triangles in the figure.

Figure 2:
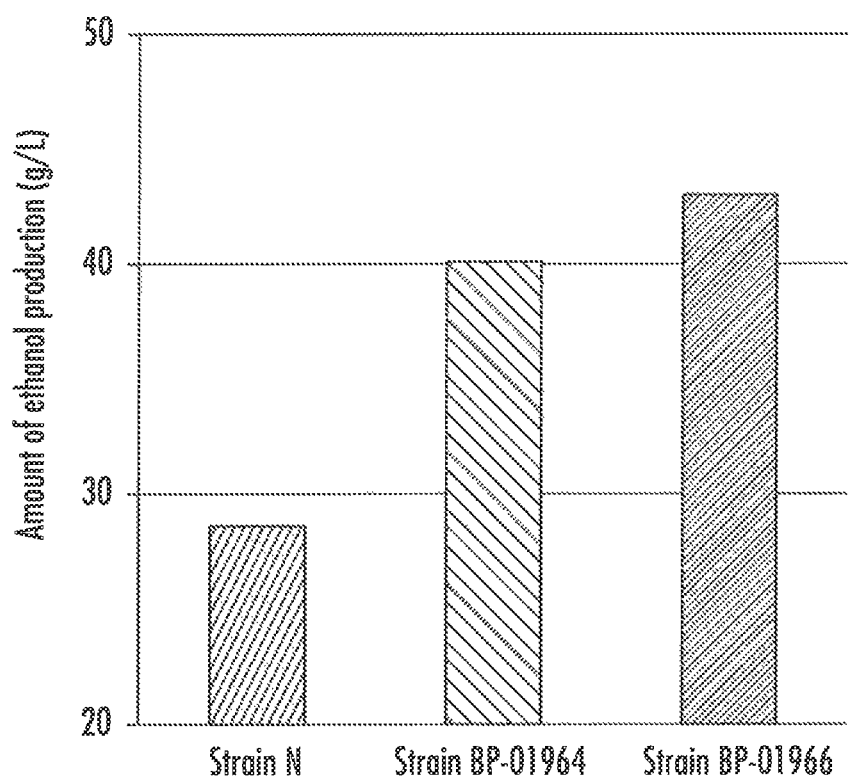
FIG. 2 illustrates ethanol production abilities of the parent strain (the strain N), the strain BP-01964, and the strain BP-01966.

Furthermore, the ethanol production ability was compared. FIG. 2 illustrates the ethanol production of the present yeast strain in comparison with the strain N (WT), the parent strain, and the yeast strain BP-01964 having a fermentation yield improved by breeding. Corn stover was treated with dilute sulphuric acid and the resultant saccharified liquid whose pH was adjusted to 6 was used. A liquid culture of the yeast strain was added so that the $OD_{600}$ of the medium became 2.0. The amount of ethanol in the culture liquid after culturing at 30° C. for 96 hours was indicated. Glucose in the saccharified solution was 63.2 g/L and xylose was 34.5 g/L. Ethanol was measured using GC-FID (manufactured by GL Sciences Inc.: GC390B).

A strain that produces ethanol more than 2.5 times as much as the wild type does and even 1.2 times as much as the strain whose ethanol production ability is increased by breeding, as apparent from FIG. 2, was obtained. Since the obtained strain has an improved ethanol production relative to the wild type strain, the obtained strain is considered to have an improved ability to utilize xylose, which is C5. Therefore, the glucose and xylose utilization abilities of the strain were examined.

2.2 Examination of Xylose Utilization Ability

Next, rice straw was treated with an ammonium aqueous solution as described above and then *Acremonium* cellulase was added to conduct enzymatic saccharification at 50° C. for 72 hours. Fermentation was conducted using the produced slurry.

The slurry fermenter has a jacket structure and the temperature was regulated by the circulation of warm water through the jacket part. Air ports are provided at the bottom and fermentation was conducted with continuously providing a predetermined amount of filtered air through the air ports at the bottom with agitation with impellers coupled with a motor.

Figure 3:
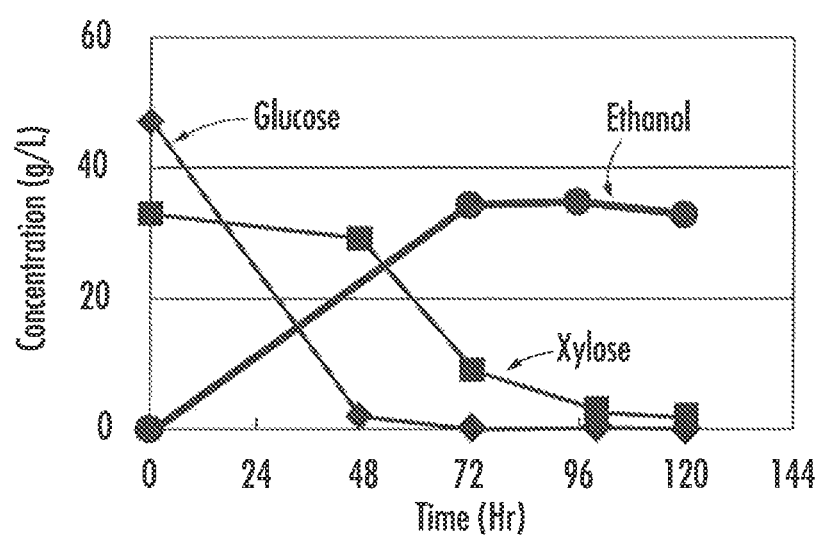
FIG. 3 illustrates glucose and xylose utilization abilities in slurry fermentation.

The change over time in amount of glucose, xylose, and ethanol contained in the slurry was analyzed. Glucose and xylose were measured by sampling and centrifuging the slurry and measuring the resultant supernatant by HPLC (manufactured by Tosoh Corporation: LC-8020). Ethanol was measured using GC-FID (manufactured by GL Sciences Inc.: GC390B) as described above. The result is shown in FIG. 3.

Glucose, which is C6, is consumed earlier, but as glucose in the slurry decreases, xylose, which is C5, is consumed to produce ethanol. Since the obtained yeast comprises both C5 and C6 utilization abilities, it can produce ethanol efficiently. Therefore, it is a strain that is also useful in industrial production.

2.3 Slurry Fermentation Ability, Clear Liquid Fermentation Ability

A yeast that efficiently carries out fermentation both with slurry and with clear liquid in the bioethanol production is preferred. Therefore, the fermentation yields with slurry and with clear liquid were compared. The fermentation yield is calculated by the following equation.

Fermentation yield=amount of obtained ethanol (g/L)/amount of glucose+xylose contained in sugar solution at the onset of fermentation (g/L)/0.5114

Figure 4:
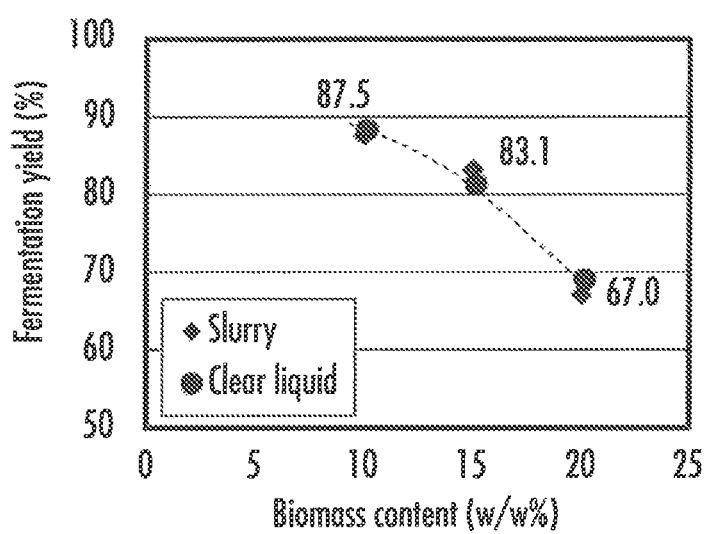
FIG. 4 illustrates fermentation yields in slurry fermentation and in clear liquid fermentation.

As illustrated in FIG. 4, the obtained strain can exhibit equivalent performance both in slurry fermentation and in clear liquid fermentation.

The yeast identified by the accession number ABP-01966 has a xylose utilization ability enhanced by breeding of the wild type *Meyerozyma guilliermondii* and can effectively produce ethanol both when using rice straw and when using corn stover as biomass, as described in the foregoing.

As described in the foregoing, a yeast strain having a xylose utilization ability enhanced by breeding of the wild type *Meyerozyma guilliermondii* and an increased ethanol production ability by genetic recombination was obtained. Furthermore, the strain can effectively produce ethanol both when using rice straw and when using corn stover as biomass.

The invention claimed is:

1. A highly efficient ethanol-fermentative yeast, the ethanol-fermentative yeast effectively producing ethanol from pentose and hexose, wherein the ethanol-fermentative yeast is a fermentative yeast having xylose utilization ability in a corn stover sugar solution improved by breeding a yeast deposited to National Institute of Technology (NITE) Patent Microorganisms Depositary under the accession number NITE ABP-01976 in a corn stover sugar solution, and wherein the fermentative yeast is deposited to NITE Patent Microorganisms Depositary under the accession number NITE BP-01966.

2. An ethanol-fermentative yeast deposited to National Institute of Technology and Evaluation (NITE) Patent Microorganisms Depositary under accession number NITE ABP-01966.

* * * * *

```
SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Meyerozyma guilliermondii

<400> SEQUENCE: 1
aaggcttggg aactttcttt                                               20

<210> SEQ ID NO 2
<211> LENGTH: 20
<212> TYPE: DNA
<213> ORGANISM: Artificial Sequence
<220> FEATURE:
<223> OTHER INFORMATION: Meyerozyma guilliermondii

<400> SEQUENCE: 2
agcaattgat gattaatttt                                               20

<210> SEQ ID NO 3
<211> LENGTH: 20
<212> TYPE: DNA
<213> ORGANISM: Artificial Sequence
<220> FEATURE:
<223> OTHER INFORMATION: Meyerozyma guilliermondii

<400> SEQUENCE: 3
atgaccaatt ctcttgaaca                                               20

<210> SEQ ID NO 4
<211> LENGTH: 20
<212> TYPE: DNA
<213> ORGANISM: Artificial Sequence
<220> FEATURE:
<223> OTHER INFORMATION: Meyerozyma guilliermondii

<400> SEQUENCE: 4
aaattgtgcc gtgtcaaact                                               20

<210> SEQ ID NO 5
<211> LENGTH: 20
<212> TYPE: DNA
<213> ORGANISM: Artificial Sequence
<220> FEATURE:
<223> OTHER INFORMATION: Meyerozyma guilliermondii

<400> SEQUENCE: 5
gttgtagcgg aggctcaatt                                               20

<210> SEQ ID NO 6
<211> LENGTH: 20
<212> TYPE: DNA
```

```
<213> ORGANISM: Artificial Sequence
<220> FEATURE:
<223> OTHER INFORMATION: Meyerozyma guilliermondii

<400> SEQUENCE: 6
tgtataattt aaatgtgggt                                              20

<210> SEQ ID NO 7
<211> LENGTH: 20
<212> TYPE: DNA
<213> ORGANISM: Artificial Sequence
<220> FEATURE:
<223> OTHER INFORMATION: Meyerozyma guilliermondii

<400> SEQUENCE: 7
atgtcaattc cagaatccat                                              20

<210> SEQ ID NO 8
<211> LENGTH: 20
<212> TYPE: DNA
<213> ORGANISM: Artificial Sequence
<220> FEATURE:
<223> OTHER INFORMATION: Meyerozyma guilliermondii

<400> SEQUENCE: 8
caccttggct ggaagtgctg                                              20
```